US005766841A

United States Patent [19]

Liav et al.

[11] Patent Number: 5,766,841

[45] Date of Patent: Jun. 16, 1998

[54] KIT FOR VISUALLY DETECTING THE PRESENCE OF A CLINICAL SPECIMEN

[75] Inventors: Avraham Liav, Denver, Colo.; Craig D. Shimasaki, Tulsa, Okla.; James F. Maher, Broken Arrow, Okla.; C. Worth Clinkscales, Tulsa, Okla.; Michael D. Roark, Owasso, Okla.

[73] Assignee: Oklahoma Medical Research Foundation, Oklahoma City, Okla.

[21] Appl. No.: 479,789

[22] Filed: Jun. 7, 1995

Related U.S. Application Data

[60] Continuation of Ser. No. 133,605, Oct. 8, 1993, abandoned, which is a division of Ser. No. 963,505, Oct. 16, 1992, Pat. No. 5,252,458, which is a continuation of Ser. No. 635,849, Dec. 31, 1990, abandoned.

[51] Int. Cl.$^6$ .................................................. C12Q 1/70
[52] U.S. Cl. ........................... 435/5; 435/18; 435/810; 435/975
[58] Field of Search .............................. 435/5, 18, 810, 435/975; 436/165

[56] References Cited

U.S. PATENT DOCUMENTS

| | | | |
|---|---|---|---|
| 3,950,322 | 4/1976 | Thomas et al. | 260/210 R |
| 4,632,901 | 12/1986 | Valkirs et al. | 435/5 |
| 4,772,553 | 9/1988 | Fujii et al. | 435/13 |
| 4,810,636 | 3/1989 | Corey | 435/14 |
| 4,877,727 | 10/1989 | Miike et al. | 435/24 |
| 5,081,017 | 1/1992 | Longoria | 435/30 |
| 5,252,458 | 10/1993 | Liav et al. | 835/5 |

FOREIGN PATENT DOCUMENTS

| | | | |
|---|---|---|---|
| 0 269 876 | 6/1988 | European Pat. Off. | |
| 0 269 876 A12 | 6/1988 | European Pat. Off. | G01N 33/52 |

OTHER PUBLICATIONS

Yolken, R., Fluorometric Assay for Measurement of Viral Neuraminidase—Application to the Rapid Detection of Influenza Virus in Nasal Wash Specimens, J of Infectious Diseases 142(4) 516–523, Oct. 1980.

Pachucki, "Early Detection of Influenza Virus by Using a Fluorometric Assay of Infected Tissue Culture", *J. of Clinical Microbiology*, vol. 26, No. 12 (Dec. 1988) pp. 2664–2666.

Yolken et al., "Fluorometric Assay for Measurement of Viral Neuraminidase—Application to the Rapid Detection of Influenza Virus in Nasal Wash Specimens", *J. of Infectious Diseases*, No. 4, (Oct. 1980) pp. 516–523.

Zbiral et al., "Synthesis of the 4–Methylumbelliferyl 2α–Glycosides of 7–Epi, 8–Epi–, and 7,8–Bis (epi)–N–acetylneuraminic Acids, as well as of the 7–Deoxy–, 8–Deoxy, 9–Deoxy, and 4,7–Dideoxy–N–acetylneuraminic Acids and Their Behaviour Towards Sialidase from Vibrio cholerae", *Liebigs, Ann. Chem.* (1989) pp. 519–526.

Zbiral et al., Structural Transformations of N–Acetylneuraminic Acid, VII. Synthesis of 7–, 8–, 9–Desoxy–and 4, 7–Didesoxyneuraminic Acid, *Monatshefte fur Chemie*, vol. 119 (1988) pp. 127–141.

Kim et al., "Enzymes in Carbohydrate Synthesis: N–Acetylneuraminic Acid Aldolase Catalyzed Reactions and Preparation of N–Acetyl–2–deoxy–D–neuraminic Acid Derivatives"*J. Am. Chem. Soc.*, vol. 110 (1988), pp. 6481–6486.

Kiyoyani et al., "Enzmological Characteristics of Avian Influenza A Virus Neuraminidase" *Microbiol. Immunol.*, vol. 31, No. 11 (1987) pp. 1131–1135.

Kiyotani et al., Enzymological Heterogeneity of Influenza B Virus Neuraminidase Demostrated by the Flurometric Assay Method, *Zbl. Bakt. Hyq.*, vol. (A260) (1985) pp. 273–285.

Kiyotani et al., "Fluorometric Measurement of Neuraminidase Activity of Influenza Viruses", *Hiroshima J. of Medical Sciences*, vol. 33, No. 2, pp. 287–292.

Yolken, "Enzyme Immunoassays for the Detection of Infectious Antigens in Body Fluids: Current Limitations and Future Prospects", *Reviews of Infectious Diseases*, vol. 4, No. 1 (1982) pp. 35–68.

Yolken, "Enzymic Analysis for Rapid Detection of Microbial Infection in Human Body Fluids: An Overview", *Clinical Chem.*, vol. 27, No. 9 (1981), pp. 1490–1498.

(List continued on next page.)

*Primary Examiner*—Ralph Gitomer
*Attorney, Agent, or Firm*—Fitch, Even, Tabin & Flannery

[57] ABSTRACT

A kit for visually detecting the presence of a virus in a direct clinical specimen is provided. The kit employs a rapid and direct assay for visually detecting a virus having a characteristic enzyme in a direct clinical sample without the need for any culturing step. This assay contains the following steps: (1) the clinical sample is contacted in solution with a substrate for the enzyme which includes a chromogen that is cleaved from the substrate by the enzyme and a precipitating agent which reacts with the liberated chromogen to form a precipitate, (2) the precipitate is concentrated, and (3) the concentrated precipitate is visually observed for the characteristic color of the chromogen. The observance of the characteristic color confirms the presence of the virus in the clinical specimen. The kit contains (a) a buffer solution for extraction of the characteristic enzyme from the clinical sample; (b) a substrate for the characteristic enzyme, where the substrate contains a chromogen that is liberated by reaction between the characteristic enzyme and the substrate, if the characteristic enzyme is present in the clinical sample; (c) a precipitating agent which reacts with the liberated chromogen in the buffer solution to produce a colored precipitate if the characteristic enzyme is present in the clinical sample; and (d) a device for concentrating the colored precipitate sufficiently to provide a distinct, visibly detectable spot of the colored precipitate if the characteristic enzyme is present in the clinical sample.

19 Claims, 1 Drawing Sheet

OTHER PUBLICATIONS

Myers et al. "The Synthesis of 4-Methylumbelliferyl α-Ketoside of N-Acetylneuraminic Acid and Its Use in a Fluorometric Assay for Neuraminidase", *Analytical Biochem.*, vol. 101, (1980), pp. 166-174.

Santer. "A Rapid Assay for Neuraminidase—the Detection of Two Differences in Acivity Associated With Virus Transformation", *Biochimica et Biophysica Acta*, vol. 523, (1978) pp. 435-442.

Beau. "Metabolism of 4-O-Methyl-N-acetylneuraminic Acid a Synthetic Sialic Acid". 1 *Eur. J. Biochem.*, vol. 106, (1980), pp. 4279-4283.

Gross et al. Interaction of N-Acetyl-4-epi-D-neuraminic Acid with Key Enzymes of Sialic Acid Metabolism. *Biochemistry*, vol. 27, (1988) pp. 4279-4283.

Hagedorn et al., "Synthesis and Biological Properties of N-Acetyl-4-deoxy-D-neuraminic Acid" *Helvetica Chimca Acta*, vol. 69 (1986) pp. 2127-2133.

Baumberger et al., "4-Methylumbelliferyl 5-Acetamido-3, 4,5-trideoxy-α-D-manno-2-nonulopyranosidonic Acid: Synthesis and Resistance to Bacterial Sialidases", *Helvetica Chimica Acta*, vol. 69, (1986), pp. 2127-2133.

Gross et al. N-Acetyl-4-deoxy-D-neuraminic Acid is Activated and Transferred on to Asialoglycoprotein, *Glyco Conjugate*, vol. 4, (1987) pp. 145-156.

Bobrow et al., "Catalyzed reporter Deposition, A Novel Method of Signal Amplification" *J. Immunol. Methods*, 125 (1989) pp. 279-285.

KIT FOR VISUALLY DETECTING THE PRESENCE OF A CLINICAL SPECIMEN

This application is a continuation of application Ser. No. 08/133,605, filed Oct. 8, 1993, now abandoned, which is a Divisional of U.S. application Ser. No. 07/963,505, filed Oct. 16, 1992, now U.S. Pat. No. 5,252,458, which is a Continuation of U.S. application Ser. No. 07/635,849, filed Dec. 31, 1990, now abandoned.

FIELD OF THE INVENTION

This invention relates to diagnostic tests for detection of viruses in clinical specimens. More specifically it relates to visual detection of the presence of a virus that has a characteristic enzyme through the reaction of the enzyme with a chromogenic substrate for the enzyme and an agent that reacts with the liberated chromogen to produce a visually detectable product.

BACKGROUND OF THE INVENTION

The rapid diagnosis of viral infections is becoming an integral part of good medical practice. Some viruses have definable antigens against which antibodies can be produced. Therefore, immunoassays have been widely used for the measurement of the antigen and thus the determination of the presence or absence of a virion. There are cases, however, where antibody-antigen reactions are too specific, and the test may not reliably diagnose a viral infection. Where it is desirable to measure a more broad group of virions, it may be possible to detect a particular structural component of the virus. For example, influenza viruses possess surface glycoproteins that have neuraminidase activity. The surface glycoproteins hydrolyze substrates that contain α-ketosidically linked N-acetylneuraminic acid. When a virion with neuraminidase activity is incubated with a chromogenically or fluorometrically modified N-acetylneuraminic acid substrate, the enzyme will cleave the chromogenic or fluorometric group from the substrate and the reaction product will indicate the presence of the virion. The enzyme, in the case of influenza is part of the virus itself, but in other cases may be produced by the virus or by cells as a direct result of the cells being infected with the particular virus.

An assay for the direct measurement of influenza neuraminidase was developed by Yolken et al., *J. Infectious Diseases* 142:516–523 (1980). Yolken used the 4-methylumbelliferyl-α-ketoside of N-acetylneuraminic acid as a fluorescent substrate to measure neuraminidase activity in preparations containing small quantities of cultivated influenza virus as well as in some nasal wash specimens from human volunteers experimentally infected with influenza virus. Yolken suggested that "successful development of fluorometric enzyme assays for the detection of influenza neuraminidase might thus provide for a practical means of influenza diagnosis that is sufficiently rapid to allow for the institution of appropriate preventative and therapeutic interventions". Id. at 522. Yolken attempted detection with colorimetric neuraminidase assays. According to Yolken, the colorimetric assays were insufficiently sensitive for clinical applications. In fact, "visual neuraminidase substrates did not detect neuraminidase in any nasal wash specimen" that Yolken studied. Id. at 520. In contrast, Yolken noted that fluorometric assays may be suitable for detecting influenza neuraminidase in clinical samples. "The successful development of fluorometric enzyme assays for the detection of influenza neuraminidase might thus provide for a practical means of influenza diagnosis that is sufficiently rapid to allow for the institution of appropriate preventative and therapeutic interventions." Id. at 522. Following up on this hypothesis, Pachucki et al., *J. Clinical Microbiology* 26:2664–666 (1988), tested the 4-methylumbelliferyl-α-ketoside of N-acetylneuraminic acid on clinical specimens collected from influenza patients. They reported that, due to its low sensitivity, the "assay was not useful in detecting neuraminidase directly in clinical specimens but identified 91% of virus-positive isolates 24 h after inoculation onto tissue culture". Id. at 2665.

The combined teachings of these references, therefore, lead away from the use of neuraminidase substrates to detect influenza neuraminidase activity in clinical samples, and further teach that visual detection is impractical for any specimen.

SUMMARY OF THE INVENTION

One aspect of the invention is a method of detecting the presence of a virus that comprises a characteristic enzyme in a clinical sample suspected of containing the virus comprising the steps of:

(a) incubating the sample with a solution of a substrate for the enzyme, said substrate comprising a reactive group that is liberated by reaction between the enzyme and the substrate and said solution containing an agent that reacts with the liberated reactive group to produce a visible reaction product, said incubation being carried out under conditions that permit the enzyme to react with the substrate to liberate the reactive group and the reactive group to react with the agent; and (b) visually observing the product of step (a) to determine the presence or absence of said visible reaction product.

Another aspect of the invention is a method of detecting the presence of a virus that comprises a characteristic enzyme in a clinical sample suspected of containing the virus comprising the steps of:

(a) incubating the clinical sample with a solution of a chromogenic substrate for the enzyme and a precipitating agent, the chromogenic group of the substrate exhibiting a characteristic color when liberated from the substrate, said incubation being carried out under conditions that permit the enzyme to react with the substrate to liberate the chromogen and the liberated chromogen to be precipitated by the precipitating agent;

(b) concentrating the precipitated chromogen; and (c) visually observing the concentrate of step (b) for the presence of said color.

Yet another aspect of the invention is a kit for use in the detection of the presence of a virus that comprises a characteristic enzyme in a clinical sample suspected of containing the virus, said kit comprising in packaged combination:

(a) a buffer solution for extraction of the clinical sample;

(b) a substrate for the enzyme, said substrate comprising a chromogen that is liberated by reaction between the enzyme and the substrate; and (c) a precipitating agent that in solution reacts with the chromogen to produce a visibly detectable colored precipitate.

BRIEF DESCRIPTION OF THE DRAWINGS

FIG. 2A provides a side view and FIG. 2B provides a top view of the concentrating means.

DETAILED DESCRIPTION OF THE INVENTION

Figure 1:
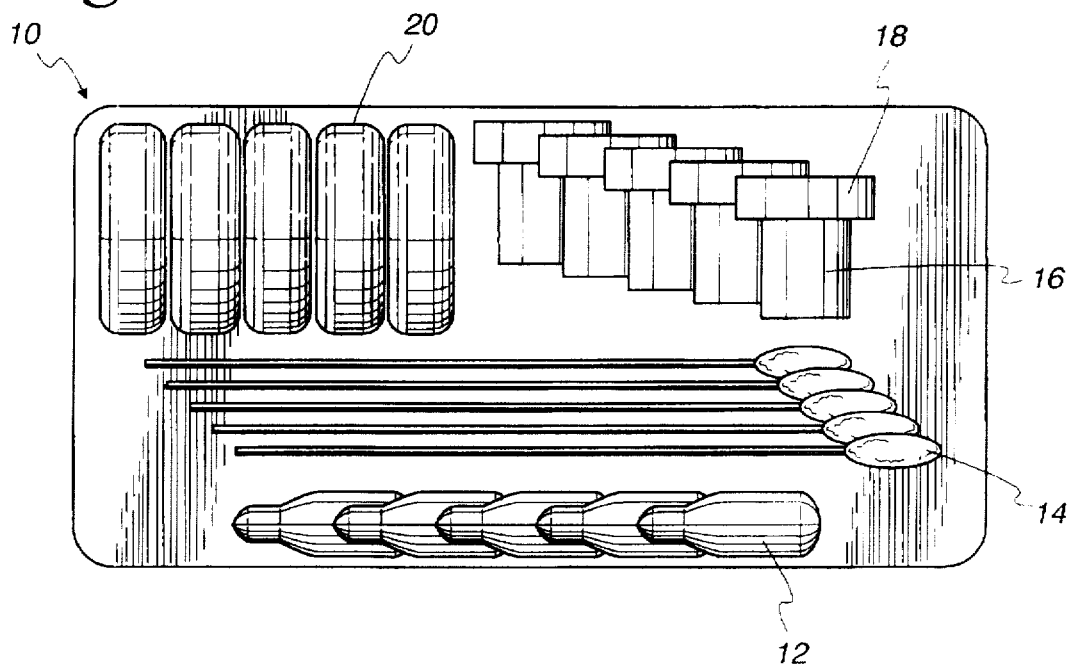
FIG. 1 generally illustrates an assay or test kit of the present invention.

The present invention may be used to detect the presence of any virus that has a characteristic enzyme. Examples of such viruses and enzymes are influenza A or B virus (neuraminidase, RNA polymerase, ribonuclease), adenovirus (protein kinase, protease endonuclease), CMV (ornithine decarboxylase, DNA polymerase, protein kinase, exonuclease), herpes simplex (DNA polymerase, protein kinase, thymidine kinase), parainfluenza (hemagglutinin-neuraminidase), and respiratory syncytial viruses (polymerase).

Substrates for these enzymes are known in the art, e.g., N-acetylneuraminic acid for neuraminidase, thymidyl phosphate for thymidine kinase, adenylphosphate for protein kinase, and ornithine for ornithine decarboxylase. These substrates may be coupled to chromogens by known chemistry. For instance, in the case of N-acetylneuraminic acid, the acid is first converted to its methyl ester by treatment in methanol with trifluoroacetic acid. Reaction of the ester in excess acetyl chloride acetates the free alcohol groups on the substrate and effects conversion to the glycosyl chloride simultaneously. The glycosyl chloride in chloroform is then reacted with an aqueous solution of the sodium salt of the chromogen in the presence of a phase transfer reagent such as triethylammonium chloride to effect coupling. Deprotection of the acetate and methyl ester groups by treatment with sodium methoxide and sodium hydroxide yields the chromogen/N-acylneuraminic acid conjugate.

The clinical samples that are tested in the invention will typically be pharyngeal, nasopharyngeal (in the case of pediatric patients) or respiratory secretions collected from patients as wash, expectorate or swab specimens.

Proper collection and handling of clinical specimens is the most important factor in a successful assay. The possibility of virus isolation is increased when specimens are collected as soon as possible (3 to 7 days) after disease onset.

In the case of influenza and depending on the type of respiratory syndrome experienced by the patient, several different specimens may be collected as outlined below.

Upper Respiratory Tract Infections

Colds are acute, self-limited viral infections of the epithelial surfaces of the upper airway characterized by nasal discharge and stuffiness, sneezing, rhinitis, and throat irritation. In infants, additional symptoms may include obstruction of the nasal passages, fever, and irritability. Low volume nasal washes (2 ml or less) and nasal aspirates usually reveal high virus titers.

Pharyngitis is an inflammatory disease of the mucous membranes and structures of the throat often involving the nasopharynx, uvula, and soft palate. Soreness and irritation are involved, but rarely is severe pain or difficulty in swallowing apparent. Additional symptoms include fever, headache, nausea, vomiting, abdominal pain, and cervical adenitis. Diagnosis requires objective evidence such as erythema, exudate, or ulceration. Malaise, myalgia, chills, dizziness, and cough are also occasionally noted. Pharyngeal swabs or nasopharyngeal aspirates should be collected, especially if nasal symptoms are prominent. Low volume throat washings or swabs may be preferable if there is prominent pharyngitis.

Lower Respiratory Tract Infections

Influenza syndrome includes fever, chills, sore throat, and systemic complaints. A cough is also associated with common cold and pharyngeal symptoms. This syndrome is most often observed during epidemics throughout the winter months. Throat swabs or washings should be collected.

Pneumonia, and infiltrative disease of the lungs is most frequently viral in nature for infants and children. Respiratory tract symptoms include cough and shortness of breath. Nasopharyngeal aspirates, tracheal aspirates, bronchial aspirates or nasal washes are preferred. Throat swabs are acceptable.

Correct collection of the above-listed specimens will help to assure a timely diagnosis. Specimen collection, processing, and culture isolation of respiratory viruses should be attempted only by experienced personnel. Nasopharyngeal swabs may not retrieve a large number of virions, but are much easier to collect, especially with infants. If secretions are too small as in the convalescent stage of croup, or the mucosa particularly fragile, nasopharyngeal swabs may be the specimen of choice. Throat swabs or washes may be combined with nasopharyngeal swabs or collected alone particularly with influenza virus infections. Nasal washes provide an easy collection method, as with swab specimens, but increase the number of mucosal cells available. Nasopharyngeal aspirates, particularly where respiratory syncytial virus (RSV) and parainfluenza virus infections are suspected, are strongly encouraged.

Nasopharyngeal swab specimens are collected as follows: A dry swab (cotton or Dacron) is inserted into one or both nostrils to the nasopharyngeal area. The swab is allowed to remain in the nostril for a few seconds to absorb secretions, rotated gently, and then withdrawn. A separate swab used for each nostril may increase the specimen volume. Swab(s) should be placed into 1 to 2 ml of aqueous buffer solution, the shaft broken off, and the cap tightly secured.

Throat swab specimens are collected as follows: A swab (cotton or Dacron), moistened in sterile phosphate buffered saline (0.15M sodium chloride and 0.01M sodium phosphate, pH 7.0–7.6), is used to vigorously rub the tonsils and the posterior pharynx. The swab is then extracted into a sterile vial containing 2 ml of aqueous buffer solution, and the vial is capped.

Throat wash specimens are collected as follows: The patient is asked to gargle with 1 to 2 ml of sterile phosphate buffered saline (0.15M sodium chloride and 0.01M sodium phosphate, pH 7.0–7.6) and the buffered saline is collected into a sterile vial containing 1 to 2 ml of aqueous buffer solution and the cap tightly secured.

Nasal wash specimens are collected as follows: 1 to 2 ml of sterile phosphate buffered saline (0.15M sodium chloride and 0.01M sodium phosphate, pH 7.0–7.6) is instilled into each nostril while the patient holds his/her head tilted back. Then the head is tipped forward and the fluid collected into a sterile vial containing 1 to 2 ml of aqueous buffer solution and the cap tightly secured.

Nasopharyngeal wash specimens are collected as follows: 1 to 2 ml of sterile phosphate buffered saline (0.15M sodium chloride and 0.01M sodium phosphate, pH 7.0–7.6) is aspirated into a soft rubber bulb. The patient is placed on his/her side in a supine position and one nostril is gently pressed closed with finger pressure. The point of the bulb is used to completely occlude the other side. The phosphate buffered saline is then squeezed into the nose and quickly aspirated. Secretions are then expelled into a sterile vial containing 1 to 2 ml of aqueous buffer solution and the cap tightly secured.

Nasopharyngeal aspirate specimens are collected as follows: A No. 8 French soft plastic feeding tube is attached through a valve-containing trap to an electric suction apparatus. The sterile catheter is introduced through the flares to the back of the nose. Suction is intermittently applied through the means of a thumb valve while the catheter is slowly withdrawn. The process may be repeated once in each nostril so that 0.2 to 0.8 ml of secretion is obtained in the trap. The secretion is then transferred to 1 to 2 ml of aqueous buffer solution and the cap tightened securely.

The aqueous buffer solution referred to in the above collection procedures preserves enzyme activity. It maintains the pH at about 4 to 7, preferably 5.5 to 6.5. The solution also contains optionally about 0.1% to 10% by weight nonionic detergent, a small amount (1–20 mM) of alkaline earth metal cation (Ca, Mg, preferably Ca), and a sufficient amount of a stabilizer selected from the group consisting of polyhydric sugar alcohols, simple sugars, and disaccharide sugars to enhance the thermal stability of the enzyme in the sample. In the case of washes and aspirates, if the specimen is to be assayed within five minutes of collection, it may be combined directly with the substrate and precipitating agent and need not be combined with buffer solution. Similarly, fresh swabs may be extracted directly into the substrate and precipitating agent solution if they are to be tested within five minutes after collection.

The buffer may be organic or inorganic. Examples of suitable buffers are conventional buffers (e.g. monosodium citrate-disodium citrate mixture, citric acid-trisodium citrate mixture, citric acid-monosodium citrate mixture, etc.), acetate buffers (e.g., acetic acid-sodium acetate mixture), succinate buffers (e.g. succinic acid-monosodium succinate mixture, succinic acid-sodium hydroxide mixture, succinic acid-disodium succinate mixture, etc.), tartrate buffers (e.g. tartaric acid-tartrate mixture, tartaric acid-potassium tartrate mixture, tartaric acid-sodium hydroxide mixture etc.), fumarate buffers (e.g. fumaric acid-monosodium fumarate mixture, fumaric acid-disodium fumarate mixture, monosodium fumaric acid-disodium fumarate mixture), gluconate buffers (e.g. gluconic acid-sodium gluconate mixture, gluconic acid-sodium hydroxide mixture, gluconic acid-potassium gluconate mixture, etc.), oxalate buffers (e.g. oxalic acid-sodium oxalate mixture, oxalic acid-sodium hydroxide mixture, oxalic acid-potassium oxalate mixture, etc.), lactate buffers (e.g. lactic acid-sodium lactate mixture, lactic acid-sodium hydroxide mixture, lactic acid-potassium lactate mixture, etc.), acetate buffers (e.g. acetic acid-sodium acetate mixture, acetic acid-sodium hydroxide mixture, etc.), malate buffers (e.g., D,L-malic acid-disodium malate mixture), phosphate buffers (e.g. monosodium phosphate-disodium phosphate mixture, monosodium phosphate-sodium hydroxide mixture, trisodium phosphate-hydrochloric acid mixture, etc.), 2-(N-morpho-lino) ethanesulfonic acid, [bis-(2-hydroxyethyl)-imino]tris (hydroxymethyl)methane, N-2-acetamido-iminodiacetic acid, 1,3-bis[tris(hydroxymethyl)methyl-amino]propane, piperazine-N,N'-bis(2-ethanesulfonic acid), N-2-acetamido-2-aminoethanesulfonic acid, 3-(N-morpholino)-2-hydroxypropanesulfonic acid, N-N-bis-(2-hydroxyethyl)2-aminoethanesulfonic acid, 3-(N-morpho-lino) propanesulfonic acid, 2-[tris(hydroxymethyl)methyl-amino] ethanesulfonic acid, N-2-hydroxyethylpiperazine-N'-2-ethanesulfonic acid, 3-{[tris-(hydroxymethyl)-methyl] amino}-2-hydroxypropanesulfonic acid.

Examples of non-ionic detergents useful in the buffer solution are the Pluronics such as Polysorbate 20 and Polysorbate 80, Triton X-100, NP-40, and alkyl glucosides such as $C_8$–$C_9$ alkyl glucoside. The detergent is an optional component and facilitates release of the enzyme from the viral envelope.

Examples of the stabilizers that are used in the buffer solution are trihydric or higher sugar alcohols, such as glycerin, erythritol, arabitol, xylitol, sorbitol, mannitol, the simple sugars glucose and fructose and the disaccharide sucrose. These polyhydric sugar alcohols, and simple and disaccharide sugars can be used alone or in combination. In order to stabilize the activity of the neuraminidase-containing viruses, the polyhydric sugar alcohols or simple and disaccharide sugars are added to the liquid formulation/ excipient system in an amount from 0.2M to 2.1M and preferably, 0.6M to 2.0M.

Once mixed with the buffer solution, the sample may be stored for prolonged periods, preferably at 2° C. to 8° C. without significant loss of enzyme activity. Repeated freezing and thawing of the sample should be avoided.

The fresh specimens (used within five minutes of collection) or the buffered stabilized specimen is then combined and incubated with a mixture of chromogenic substrate and precipitating agent appropriate to detect the virus via the enzyme associated with the virus. The reaction is carried out between ambient and physiological (approximately 20°–40° C.), preferably at room temperature. Higher temperatures may be used, but they may produce false positives. The sensitivity of the test at physiological temperature is substantially greater than at ambient temperatures. The reaction time will normally be in the range of 20 to 120 minutes, more usually 30 to 60 minutes. The chromogenic substrate concentration will normally range from 0.05 mM to 5.0 mM, preferably 0.05 mM to 0.3 mM. If there is enzyme activity in the sample, the chromogenic group will be cleaved from the substrate and the liberated chromogen will react with the precipitating agent to form a precipitate having a characteristic color.

The agents that allow for precipitation and visual detection of the chromogen may be salts, dyes or color-producing compounds that can be in their activated or inactive state whereby upon activation they will produce the precursor to the final colored compound. These dyes or color-producing compounds include any compounds which will couple to, or react with the liberated chromogen, but not limited to the diazonium salts listed below. Diazonium salts are formed by the reaction of a precursor amine with a nitrite. Thus, the aryl amine precursors to diazonium salts may be used in combination with an alkyl nitrite, e.g., n-butyl nitrite and t-butyl nitrite, at an acid pH. For maximum stability the diazonium salt and substrate are preferably maintained in a dry (e.g., lyophilized) form prior to use. The concentration of the diazonium salt, dye, or color producing compound will typically range between 0.01 mM to 10 mM with optimum ranges between 0.05 mM to 0.5 mM. Concentrations between 0.025 mM to 5 mM have been tested with several diazonium salts and results indicate that with increasing concentrations of these diazonium salts sensitivity can be increased to an optimal point.

The preferred aryl alcohol chromogens and their characteristic colors when detected visually or colorimetrically after precipitation by a diazonium salt are listed in the following table. The colors were determined by the interaction of 0.2 mM indicated diazonium salt solution with a 0.2 mM free indicated chromogen solution in a 50 mM sodium acetate buffer at pH 5.9 and allowing the reaction to proceed for several minutes and collecting the precipitate on a 0.45 micron nitrocellulose membrane.

| | INTERACTING DIAZONIUM SALT | | | | | | |
|---|---|---|---|---|---|---|---|
| Released* Chromogen | Fast Black K | Fast Red-Violet LB | Fast Red ITR | Fast Red AL | Fast Corinth V | Fast Blue BB | Fast Violet B |
| MOP | brown | yellow-orange | sand | burnt orange | maroon | mauve | peach |
| DMP | brown-black | red-orange | peach | dark peach | dark purple | red | orange |
| 6BN | dark brown | red | orange | burnt orange | dark purple | purple | maroon |
| 3AAP | tan | yellow | yellow | peach | dark peach | sand | yellow |
| 3BP | tan | yellow | sand | beige | burnt orange | none | none |
| 4CN | black | brown | berry | sienna brown | black | brown-black | brown |
| CONTROL (no chromogen) | flesh | none | none | ivory | flesh | none | none |

*The released chromogens in solution at the indicated concentrations produced no color.
MOP = 3-methoxyphenol; DMP = 3-dimethylaminophenol; 6BN = 6-bromo-2-naphthol; 3AAP = 3-acetamidophenol; 3BP = 3-bromophenol; 4CN = 4-chloro-1-naphthol.

In addition to the substrate and precipitating agent, the reaction mixture may contain color enhancing agents and moieties required for enzymatic activity. In this regard, thimerosol (at 0.1% to 0.5% by weight) and methyl paraben or propyl paraben (at 0.01% by weight) were found to enhance the color of the precipitate formed from several of the above-listed diazonium malts. Calcium ion has been found to greatly increase the enzyme turnover rate and is thus a desirable component of the mixture. Calcium ion may be added as a salt, e.g., calcium chloride, preferably at concentrations in the range of 5–20 mM, preferably 10 mM. Uncoupled chromogens may be included to provide contrasting color which would distinguish a positive test from a negative test. Bulking or stabilizing agents such as mannitol may also be added to the substrate and salt.

The volume of the sample used in the assay may affect the sensitivity and the presence of background color. Assay volumes ranging between 0.25 ml and 2.0 ml have been used successfully. Concentrations of substrate and precipitating agent should be adjusted to give optimum results for each assay volume. In this regard, it was found that when the assay volume is increased (i.e., concentration of enzyme is decreased) the concentrations of substrate and precipitating agent must be decreased to reduce undesirable background color formation.

The liberation of chromogen and the formation of precipitate are pH dependent, and the optimum pH for each of these reactions may differ. Generally the pH may range between about 3 and 9, preferably between 5 and 8. In tests using a panel of two chromogens and three diazonium salts, the most intense color was produced at pH 6.9.

It may be desirable to improve the detection limit afforded by the present invention for various samples. In such a case, an enzyme amplification technique described by Bobrow et al., Journal of Immunological Methods, 125:279–285 (1989), may be useful. The method involves "utilizing the ADRE (analyte dependent reporter enzyme) of a solid-phase assay to catalyze the deposition of additional reporter enzyme onto the solid phase, resulting in signal amplification and improved assay detection limits". Id. at 280.

The colored precipitate that is produced may be concentrated by any conventional liquid-solid separation means, such as filtration, evaporation, and centrifugation, so that it may be more readily seen. Preferably the reaction medium is filtered using a suitable filter with a pore size small enough to retain the precipitate. Pore sizes will typically range between 0.20 microns and 20 microns, preferably from 0.45 microns to 5 microns. Examples of suitable filter materials are nylon, chemically modified nylon, nitrocellulose and hybrid nitrocellulose. The reaction medium may be passed through the filter by gravitation or under positive force, such as that effected by positive pressure, vacuum or capillary action. In the latter an absorbent porous material, such as cotton or cellulose, is placed beneath and in contact with the membrane. Such material is capable of wicking and retaining the fluid volume in the reaction mixture. The reaction mixture may be focused on a small spot on the membrane to provide a distinct colored spot on the surface of the membrane indicating a positive test. The sensitivity of the assay may be increased by focusing the mixture through a small diameter spot so as to concentrate the color in a small area. The spot diameter will normally range between 1 and 5 mm.

The invention further provides a kit for use in the clinic or physician's office for rapidly detecting the presence of a virus in a clinical sample. A preferred embodiment kit comprises a vessel that contains a buffer solution wherein the sample can be deposited. The kit further contains a second sealed vessel that contains the substrate coupled to the chromogen and the precipitating agent in dry form. When the sample is deposited in the buffer solution (or the buffer solution is used to dissolve the substrate and precipitating agent), the contents of the sealed vessel are added and the solution is covered and allowed to incubate for a period as described previously. The cover for the buffer vessel is a filtration device comprising a porous membrane and absorbent material. The center portion contains a 2 cm diameter circular opening such that when the device is placed over the vessel, the vessel is sealed from the outside air. The filtration device further comprises a focusing device (e.g., a funnel) such that when the sample is deposited on the membrane by inversion of the vessel and filtration device combination, the solution is physically concentrated to a spot on the membrane which is between 1.5 and 5.0 mm. After the incubation period is completed, the vessel and filtration device are inverted to permit the reaction mixture to pass through the membrane and where virus is present, a colored reaction product will be present on the spot surface of the membrane.

The kit will also normally include positive and negative control specimens and written instructions for carrying out the assay.

Figure 2A:
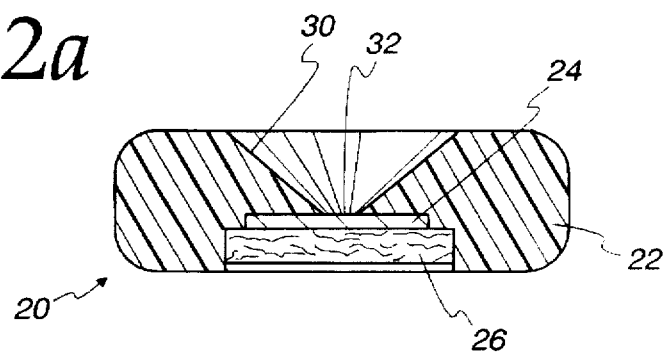
FIGS. 2A and 2B generally illustrates a means for concentrating the precipitate.
Figure 2B:
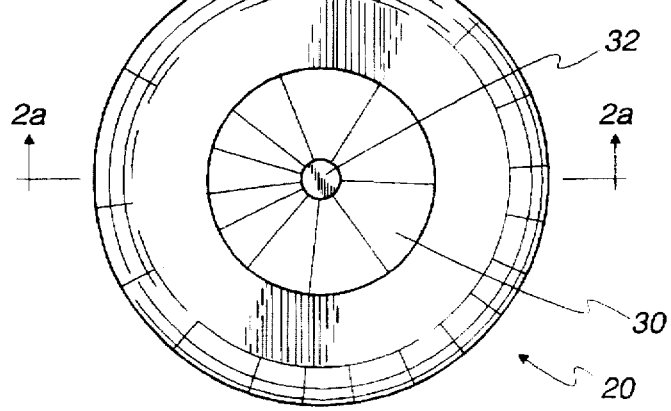

FIG. 1 generally illustrates one embodiment of the kit 10 of the present invention, which kit 10 consists of a plurality of first sealed vessels 12 containing a buffer solution and other liquid or dissolved components, a plurality of second vessels 16 sealed with caps 18 containing the substrate coupled to the chromogen and the precipitating agent in dry form, a plurality of filtration devices 20, and a plurality of swabs 14 for collection of the clinical samples. The kit may also contain an instruction booklet or other printed information (not shown) describing the use of the kit. The kit 10 shown in FIG. 1 has five each of the various components and can, therefore, be used to analyze five clinical samples. FIG. 2 illustrates the filtration device 20 of FIG. 1 in more detail. FIG. 2A shows a side view and FIG. 2B a top view of device 20. This filtration device 20 has a body 22 which contains a porous membrane 24, absorbent material 26, and a funneling device 30 to direct and focus the incubated mixture to a controlled spot or location 32 on the porous membrane 24.

In use, the contents of one vessel 12 are used to reconstitute the dry reagents of one vessel 16. A clinical sample is collected using a single swab 14 (or other appropriate collection means). The swab 14 (or other appropriate means) is then used to deposit or introduce the clinical sample directly into the reconstituted solution in vessel 16. The mixture in vessel 16 is then sealed with cap 18 and allowed to incubate for the desired time period. The sample could, of course, be incubated in any suitable vessel if desired. After incubation is complete, cap 18 is removed and the contents of vessel 16 are poured or otherwise deposited into the funneling device 30 in filtration device 20 such that the porous membrane 24 acts as a filter. Any colored precipitate formed is collected on spot 32 of porous membrane 24 and the fluid is wicked away by absorbent material 26. The presence or absence of a particular colored precipitate at spot 32 is then used to indicated the presence or absence of the particular virus. Thus, once the incubated sample is introduced into the filtration device 20, the funneling device 30 will force or guide the colored precipitate (if formed) to collect on spot 32, thereby increasing the sensitivity of the analysis.

As those skilled in the art will realize, other embodiments of the kit 10 and the filtration device 20 can be employed in the practice of this invention.

Accordingly, the present invention provides a simple and rapid technique for detecting the presence of a virus in a clinical specimen that may be carried out in the clinic or physician's office and enable the physician to prescribe the appropriate therapy to treat the infection and/or the appropriate prophylactic treatment to persons in close contact with the infected patient.

The following example further illustrates the invention. This example is not intended to limit the invention in any manner.

EXAMPLE

Clinical specimens from patients suspected of having influenza are collected as described above. The specimen is combined with an aqueous solution of 2.0 ml containing 10 mM $CaCl_2$, 3.5 mM malic acid, pH 5.9 and 0.01% Thymerosol. The combination of the specimen and aqueous solution are used to reconstitute a dry reagent mixture containing 0.075 mM 4-chloro-1-naphthol-N-acetyl-neuraminic acid, 0.05 mM Fast Red ITR, 0.04 mM 3AAP, 1% mannitol, and 21.5 mM malic acid diazonium salt in a sterile vial.

Except in the case of wash or aspirate specimens where 2 ml wash or aspirate itself are added directly to the dry reagents mixture.

After combining the specimen with the substrate mixture, the vial is capped and the mixture is incubated at 37° C. for 60 minutes.

The entire contents of the vial are then placed on a nitrocellulose filter (1.2 microns, Micron Separation, Inc.) backed with a pad of cellulose acetate (4.9×29.2×30.7 mm). The contents are focused onto the filter through a 2 mm diameter orifice.

The color of the 2 mm spot through which the contents have been filtered is observed immediately after all the solution has been absorbed through the filter. A red, pink, or orange colored spot is positive: a yellow colored spot is negative.

Modifications of the above described modes for carrying out the invention that are obvious to those of skill in the fields of virology, biochemistry, organic chemistry, diagnostic medicine and related fields are intended to be within the scope of the following claims.

We claim:

1. A kit for the detection of the presence of a virus in a direct clinical sample suspected of containing the virus, wherein the virus has a characteristic enzyme, said kit comprising;

(a) a buffer solution for extraction of the characteristic enzyme from the direct clinical sample;

(b) a substrate for the characteristic enzyme, said substrate comprising a chromogen that is liberated upon incubation of the direct clinical sample with the substrate by reaction between the characteristic enzyme and the substrate, if the characteristic enzyme is present in the direct clinical sample;

(c) a precipitating agent which reacts with the liberated chromogen in the buffer solution to produce a colored precipitate if the characteristic enzyme is present in the direct clinical sample; and (d) a means for concentrating the colored precipitate sufficiently to provide a distinct, visibly detectable spot of the colored precipitate if the characteristic enzyme is present in the direct clinical sample;

wherein the virus is selected from the group consisting of influenza A, influenza B, adenovirus, cytomegalovirus, herpes simplex, parainfluenza, and respiratory synctical virus.

2. The kit of claim 1 wherein the means for concentrating comprises a porous membrane having a pore size capable of retaining the precipitate and an absorbent pad beneath and in contact with the membrane, said pad being capable of wicking away fluid from the membrane.

3. The kit of claim 2 wherein the pore size is from about 0.2 microns to about 20 microns.

4. The kit of claim 3 wherein the pore size is from about 0.45 microns to about 5 microns.

5. The kit of claim 2 wherein the concentration means further comprises a focusing device to focus the precipitate on a small spot on the porous membrane.

6. The kit of claim 5 wherein the small spot upon which the precipitate is focused is about 1 to 5 mm in diameter.

7. The kit of claim 1 further comprising at least one control specimen selected from the group consisting of a positive control specimen and a negative control specimen.

8. The kit of claim 1 wherein the chromogen is selected from the group consisting of 3-methoxyphenol, 3-dimethylaminophenol, 6-bromo-2-naphthol, 4-chloro-1-naphthol, 3-bromophenol, and 3-acetamidophenol.

9. The kit of claim 1 wherein the precipitating agent is selected from the group consisting of Fast Red ITR, Fast Red AL, Fast Violet B, Fast Red-Violet LB, Fast Black K, Fast Blue BB, and Fast Corinth V.

10. The kit of claim 1 wherein the virus is influenza virus and the enzyme is neuraminidase.

11. A kit for detecting the presence of an influenza virus in a direct clinical sample suspected of containing the influenza virus, wherein the influenza virus has a characteristic neuraminidase enzyme and wherein the direct clinical sample is collected by means of a nasopharyngeal swab, a throat swab, a throat wash, a nasal wash, a nasopharyngeal wash, or a nasopharyngeal aspirate, said kit comprising:

(a) a buffer solution for extraction of the characteristic neuraminidase enzyme from the direct clinical sample;

(b) a substrate for the characteristic neuraminidase enzyme, said substrate comprising a chromogen that is liberated upon incubation of the direct clinical sample with the substrate by reaction between the characteristic neuraminidase enzyme and the substrate, if the characteristic neuraminidase enzyme is present in the direct clinical sample;

(c) a precipitating agent which will react with the liberated chromogen in the buffer solution to produce a colored precipitate if the characteristic neuraminidase enzyme is present in the direct clinical sample; and (d) a means for concentrating the colored precipitate sufficiently to provide a distinct, visibly detectable spot of the colored precipitate if the characteristic neuraminidase enzyme is present in the direct clinical sample.

12. The kit of claim 11 wherein the means for concentrating comprises a porous membrane having a pore size capable of retaining the precipitate and an absorbent pad beneath and in contact with the membrane, said pad being capable of wicking away fluid from the membrane.

13. The kit of claim 12 wherein the pore size is from about 0.2 microns to about 20 microns.

14. The kit of claim 13 wherein the pore size is from about 0.45 microns to about 5 microns.

15. The kit of claim 12 wherein the concentration means further comprises a means to focus the precipitate on a small spot on the porous membrane.

16. The kit of claim 15 wherein the small spot upon which the precipitate is focused is about 1 to 5 mm in diameter.

17. The kit of claim 11 further comprising positive and negative control specimens.

18. The kit of claim 11 wherein the chromogen is selected from the group consisting of 3-methoxyphenol, 3-dimethylaminophenol, 6-bromo-2-napththol, 4-chloro-1-naphthol, 3-bromophenol, and 3-acetamidophenol.

19. The kit of claim 11 wherein the precipitating agent is selected from the group consisting of Fast Red ITR, Fast Red AL, Fast Violet B, Fast Red-Violet LB, Fast Black K, Fast Blue BB, and Fast Corinth V.

* * * * *

UNITED STATES PATENT AND TRADEMARK OFFICE
CERTIFICATE OF CORRECTION

PATENT NO. : 5,766,841
DATED : June 16, 1998
INVENTOR(S) : Liav et al.

It is certified that error appears in the above-indentified patent and that said Letters Patent is hereby corrected as shown below:

On the title page item [54], and column 1 change the title as follows: After "Presence of a", insert -- Virus in a --.

Signed and Sealed this

First Day of September, 1998

Attest:

BRUCE LEHMAN

*Attesting Officer*  *Commissioner of Patents and Trademarks*